United States Patent
Wang et al.

(10) Patent No.: US 7,339,666 B2
(45) Date of Patent: *Mar. 4, 2008

(54) LIGHT-AMPLIFYING STRUCTURES AND METHODS FOR SURFACE-ENHANCED RAMAN SPECTROSCOPY

(75) Inventors: Shih-Yuan Wang, Palo Alto, CA (US); Zhiyong Li, Palo Alto, CA (US); M. Saif Islam, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 413 days.

This patent is subject to a terminal disclaimer.

(21) Appl. No.: 10/942,079

(22) Filed: Sep. 14, 2004

(65) Prior Publication Data

US 2006/0055921 A1    Mar. 16, 2006

(51) Int. Cl.
*G01J 3/44*    (2006.01)
(52) U.S. Cl. .................................................. 356/301
(58) Field of Classification Search ............ 356/301
See application file for complete search history.

(56) References Cited

U.S. PATENT DOCUMENTS

| | | | |
|---|---|---|---|
| 4,547,801 A | 10/1985 | Haisma et al. | |
| 4,674,878 A | 6/1987 | Vo-Dinh | |
| 4,903,272 A | 2/1990 | Simic-Glavaski | |
| 5,017,007 A | 5/1991 | Milne et al. | |
| 5,187,461 A | 2/1993 | Brommer et al. | |
| 5,216,686 A | 6/1993 | Holm et al. | |
| 5,255,067 A | 10/1993 | Carrabba et al. | |
| 5,256,596 A | 10/1993 | Ackley et al. | |
| 5,293,392 A | 3/1994 | Shieh et al. | |
| 5,317,587 A | 5/1994 | Ackley et al. | |
| 5,335,240 A | 8/1994 | Ho et al. | |
| 5,359,618 A | 10/1994 | Lebby et al. | |
| 5,440,421 A | 8/1995 | Fan et al. | |
| 5,468,656 A | 11/1995 | Shieh et al. | |
| 5,471,180 A | 11/1995 | Brommer et al. | |
| 5,527,712 A | 6/1996 | Sheehy | |
| 5,600,483 A | 2/1997 | Fan et al. | |
| 5,609,907 A | 3/1997 | Natan | |
| 5,677,924 A | 10/1997 | Bestwick | |
| 5,682,401 A | 10/1997 | Joannopoulos et al. | |
| 5,684,817 A | 11/1997 | Houdre et al. | |
| 5,706,306 A | 1/1998 | Jiang et al. | |
| 5,739,945 A | 4/1998 | Tayebati | |
| 5,771,253 A | 6/1998 | Chang-Hasnain et al. | |
| 5,774,485 A | 6/1998 | Stein | |
| 5,784,400 A | 7/1998 | Joannopoulos et al. | |
| 5,837,552 A | 11/1998 | Cotton et al. | |

(Continued)

OTHER PUBLICATIONS

Shubin et al., "Surface-Plasmon-Enhanced Radiation Effects in Confined Photonic Systems", Nov. 1999, IEEE Journal of Lightwave Technology, vol. 17, pp. 2183-2190.*

(Continued)

*Primary Examiner*—Gregory J. Toatley, Jr.
*Assistant Examiner*—Kara Geisel (57) ABSTRACT

Structures for amplifying light include a resonant cavity in which an analyte may be positioned. The structures for amplifying light may be used to amplify the incident light employed in surface enhanced Raman spectroscopy (SERS). SERS systems employing the structures for amplifying light of the present invention and methods of performing SERS are also disclosed.

32 Claims, 7 Drawing Sheets

U.S. PATENT DOCUMENTS

| | | | |
|---|---|---|---|
| 5,990,850 | A | 11/1999 | Brown et al. |
| 5,997,795 | A | 12/1999 | Danforth et al. |
| 5,998,298 | A | 12/1999 | Fleming et al. |
| 6,058,127 | A | 5/2000 | Joannopoulos et al. |
| 6,134,043 | A | 10/2000 | Johnson et al. |
| 6,141,360 | A | 10/2000 | Kinugawa et al. |
| 6,149,868 | A | 11/2000 | Natan et al. |
| 6,154,591 | A | 11/2000 | Kershaw |
| 6,274,293 | B1 | 8/2001 | Gupta et al. |
| 6,339,030 | B1 | 1/2002 | Constant et al. |
| 6,343,180 | B1 | 1/2002 | Kim |
| 6,396,083 | B1 | 5/2002 | Ortiz et al. |
| 6,406,777 | B1 | 6/2002 | Boss et al. |
| 6,525,880 | B2 | 2/2003 | Flanders et al. |
| 6,546,029 | B2 | 4/2003 | Sirbu et al. |
| 6,608,685 | B2 | 8/2003 | Wood et al. |
| 6,608,716 | B1 | 8/2003 | Armstrong et al. |
| 6,623,977 | B1 | 9/2003 | Farquharson et al. |
| 6,649,683 | B2 | 11/2003 | Bell |
| 6,650,675 | B2 | 11/2003 | Sahara et al. |
| 6,678,289 | B2 | 1/2004 | Kim |
| 6,700,910 | B1 | 3/2004 | Aoki et al. |
| 6,711,200 | B1 | 3/2004 | Scherer et al. |
| 2002/0068018 | A1 | 6/2002 | Pepper et al. |
| 2002/0142480 | A1 | 10/2002 | Natan |
| 2002/0182716 | A1* | 12/2002 | Weisbuch et al. ........ 435/287.2 |
| 2003/0120137 | A1 | 6/2003 | Pawluczyk |
| 2004/0063214 | A1* | 4/2004 | Berlin et al. ................ 356/301 |
| 2004/0142484 | A1 | 7/2004 | Berlin et al. |
| 2005/0032235 | A1* | 2/2005 | Tummala et al. ........... 436/171 |

OTHER PUBLICATIONS

Blanco, Alvaro, et al., "Large-sclae synthesis of a silicon photonic crystal with a complete three-dimensional bandgap near 1.5 micrometres," Letters to Nature, Nature, vol. 405, May 25, 2000, pp. 437-440.

Campbell, M., et al., "Fabrication of photonic crystals for the visible spectrum by holographic lithography," Letters to Nature, Nature, vol. 404, Mar. 2, 2000, pp. 53-56.

Chang-Hasnain, Connie J., "Tunable VCSEL," IEEE Journal on Selected Topics in Quantum Electronics, vol. 6, No. 6, Nov./Dec. 2000, pp. 978-987.

Emory, Steven R., et al., "Screening and Enrichment of Metal Nanoparticles with Novel Optical Properties," J. Phys. Chem. B, 1998, 102, pp. 493-497.

Joannopoulos, J.D., et al., "Photonic crystals: putting a new twist on light," Nature, vol. 386, Mar. 13, 1997, pp. 143-149.

Johnson, Steven G., et al., Introduction to Photonic Crystals: Block's Theorem, Band Diagrams, and Gaps (But No Defects), Feb. 3, 2003, pp. 1-16.

Kneipp., Katrin, et al., Single Molecule Detection Using Surface-Enhanced Raman Scattering (SERS), Physical Review Letters, vol. 78, No. 9, Mar. 3, 1997, pp. 1667-1670.

Lalanne, Ph., et al., "Two physical mechanisms for boosting the quality factor to cavity volume ratio of photonic crystal microcavities," Optics Express, Feb. 9, 2004, vol. 12, No. 3, pp. 458-467.

Michaels, Amy M., et al., "Surface Enhanced Raman Spectroscopy of Individual Rhodamine 6G Molecules on Large Ag Nanocrystals," J. Am. Chem. Soc., 1999, 121, pp. 9932-9939.

Qi, Minghao, et al., "A three-dimensional optical photonic crystal with designed point defects," Letters to Nature, Nature, vol. 429, Jun. 3, 2004, pp. 538-542.

Tao, Andrea, et al., "Langmuir-Blodgett Silver Nanowire Momolayers for Molecular Sensing Using Surface-Enhanced Raman Spectroscopy," Nano Letters, vol. 3, No. 9, 2003, pp. 1229-1233.

Vlasov, Yuril A., et al., "On-chip natural assembly of silicon photonic bandgap crystals," Letters to Nature, Nature, vol. 414, Nov. 15, 2001, pp. 289-293.

Fainstein A et al—"Raman Scattering Enhancement by Optical Confinement in a Semiconductor Planar Microcavity"-Physical Review Letters vol. 75, No. 20 Nov. 13, 1995 pp. 3764-3767.

* cited by examiner

LIGHT-AMPLIFYING STRUCTURES AND METHODS FOR SURFACE-ENHANCED RAMAN SPECTROSCOPY

FIELD OF THE INVENTION

The present invention relates to Raman spectroscopy chemical analysis. More particularly, the present invention relates to devices, systems, and methods for increasing the intensity of the excitation radiation in surface-enhanced Raman spectroscopy (SERS).

BACKGROUND OF THE INVENTION

Raman spectroscopy is a well-known spectroscopic technique for performing chemical analysis. In conventional Raman spectroscopy, high intensity monochromatic light provided by a light source, such as a laser, is directed onto an analyte (or sample) that is to be chemically analyzed. The analyte may contain a single molecular species or mixtures of different molecular species. Furthermore, Raman spectroscopy may be performed on a number of different types of molecular configurations, such as organic and inorganic molecules in either crystalline or amorphous states.

The majority of the incident photons of the light are elastically scattered by the analyte molecule. In other words, the scattered photons have the same frequency, and thus the same energy, as the photons that were incident on the analyte. However, a small fraction of the photons (i.e., 1 in $10^7$ photons) are inelastically scattered by the analyte molecule. These inelastically scattered photons have a different frequency than the incident photons. This inelastic scattering of photons is termed the "Raman effect." The inelastically scattered photons may have frequencies greater than, or, more typically, less than the frequency of the incident photons. When an incident photon collides with a molecule, energy may be transferred from the photon to the molecule, or from the molecule to the photon. When energy is transferred from the photon to the molecule, the scattered photon will then emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will then emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). By plotting the frequency of the inelastically scattered Raman photons against intensity, a unique Raman spectrum is obtained, which corresponds to the particular analyte. This Raman spectrum may be used for many purposes, such as identifying chemical species, identifying chemical states or bonding of atoms and molecules, and even determining physical and chemical properties of the analyte.

Since the intensity of the Raman scattered photons is low, very intense laser light sources are usually employed to provide the excitation radiation. Another Raman spectroscopy technique called Surface Enhanced Raman Spectroscopy (SERS) has been developed to increase the Raman signal produced by an analyte and to allow surface studies of the analyte. In SERS, the analyte molecules are adsorbed onto or positioned near a specially roughened metal surface. Typically, the metal surface is made from gold, silver, copper, platinum, palladium, aluminum, or other metals or metal alloys. SERS has also been performed employing metallic nanoparticles or nanowires for the metal surface, as opposed to a roughened metallic surface. The intensity of the Raman scattered photons from a molecule adsorbed on such a metal surface is typically about $10^4$-$10^6$ greater than conventional Raman Spectroscopy and can be as high as $10^8$-$10^{14}$. In other words, more photons are inelastically scattered by the analyte molecules in SERS compared to conventional Raman spectroscopy.

The surface enhancement of the Raman signal in SERS is currently attributed to two primary mechanisms: electromagnetic field enhancement and chemical enhancement, electromagnetic field enhancement being the dominant mechanism. The enhancement of the Raman signal is at least partially dependent on the surface roughness or surface features of the metal surface. In SERS, a strong electromagnetic field is present in the areas adjacent to and near the metallic surface, which is experienced by the analyte. This strong electromagnetic field enhances the Raman signal emitted from the analyte, which is, at least in part, proportional to the square of the enhanced electromagnetic field. Thus, SERS may be used to perform, for example, surface studies and studies of monolayers of materials adsorbed on metals. While SERS is an effective chemical analysis tool, it requires rather large and powerful laser light sources. A typical SERS system occupies a large table and is not particularly portable.

Accordingly, there is a need for a more compact and portable SERS system. There is also a need for a light source that requires less power during operation that also will enhance, simultaneously, the intensity of the Raman signal to enable more sensitive chemical analysis.

BRIEF SUMMARY OF THE INVENTION

The present invention relates to devices, systems, and methods for increasing the intensity of the excitation radiation in surface-enhanced Raman spectroscopy (SERS).

In one aspect of the present invention, a structure for amplifying light used in SERS is disclosed. The structure includes a first portion having a first surface and an opposing second surface. The structure further includes a second portion having a face opposing the first surface of the first portion with a resonant cavity provided therebetween. A SERS-active structure is disposed between the first portion and the second portion within the resonant cavity.

In another aspect of the present invention, a SERS system is disclosed. The SERS system includes a light amplifying structure. The light amplifying structure includes a first portion having a first surface and an opposing second surface. The light amplifying structure further includes a second portion having a face opposing the first surface of the first portion with a resonant cavity provided therebetween. A SERS-active structure is disposed between the first portion and the second portion within the resonant cavity. The system also includes a light source configured to irradiate light onto a surface of the light amplifying structure and a detector configured to receive Raman scattered light scattered by an analyte when the analyte is located within the resonant cavity adjacent the SERS-active structure.

In yet another aspect of the present invention, a method of performing SERS is disclosed. The method includes providing a radiation amplifying structure comprising means for amplifying radiation and a SERS-active structure located near the means; providing an analyte adjacent the SERS-active structure; irradiating a surface of the radiation amplifying structure with incident radiation; amplifying the intensity of the incident radiation with the means for amplifying radiation to produce amplified radiation, the amplified radiation irradiating the SERS-active structure and the analyte so as to effect Raman scattering of the amplified radiation by the analyte; and detecting the Raman scattered radiation.

These features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes structures that increase or amplify the intensity of excitation radiation incident on an analyte in Surface Enhanced Raman Spectroscopy (SERS), systems that include such structures, and methods of using the same. The term "amplify" is used in its broadest sense herein as meaning to increase or make greater, such as increasing the intensity of light within a cavity.

Structures having Fabry-Perot resonant cavities therein, or cavities formed in photonic crystals therein, can be used to increase the intensity of radiation within the cavity. A SERS sample to be analyzed (referred to herein as an "analyte") may be positioned within one of these cavities to subject it to the amplified radiation. Fabry-Perot resonant cavities and cavities formed in photonic crystals may amplify radiation of only specific wavelengths, which are at least partly determined by the physical dimensions of the resonant cavity.

Figure 1A:
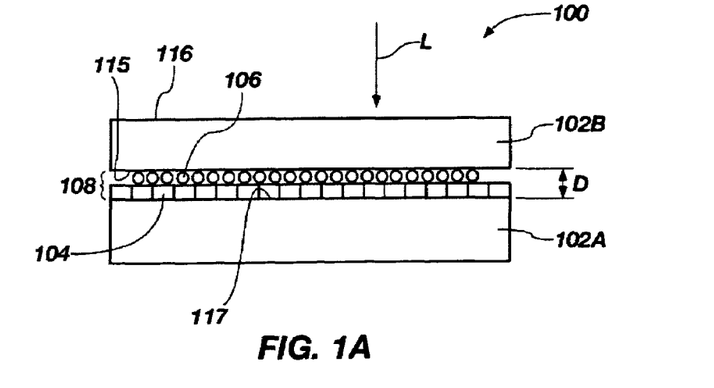
FIG. 1A is a sectional view of an exemplary light amplifying structure.

An exemplary light amplifying structure 100 is shown in FIG. 1A. The light amplifying structure 100 includes a bottom layer 102A and a top layer 102B that are separated by a distance D to define a standoff or resonant cavity 108 therebetween. The top layer 102B has a lower surface 115 and an upper surface 116 that are generally parallel to each other. Bottom layer 102A has a face 117 opposing the lower surface 115 of the top layer 102B and is separated therefrom by a distance D. A SERS-active structure 104 may be provided between the bottom layer 102A and the top layer 102B within the resonant cavity 108. An analyte 106 may be provided on the SERS-active structure 104 when performing SERS. The distance D may be as small as about a monolayer of the analyte 106 being analyzed or more.

The thickness of the bottom layer 102A and the top layer 102B may be between about 0.1 microns and about 10 microns. The length and width of the bottom layer 102A and the top layer 102B are not critical, but may be sized to allow the structure to be handled manually, for example, with tweezers or any other suitable micromanipulator device. The bottom layer 102A and the top layer 102B may be formed from a variety of different materials. Exemplary materials for the bottom layer 102A and the top layer 102B include diamond, silicon nitride, silicon dioxide, or any other suitable material. However, the bottom layer 102A and the top layer 102B should be at least partially transparent to the wavelength of the incident excitation radiation to be used for spectroscopic analysis.

The SERS-active structure 104 located within the resonant cavity 108 is used to enhance the Raman signal produced by photons that are inelastically scattered by the analyte 106 during analysis. The SERS-active structure 104 may be used to effect electromagnetic enhancement of the Raman signal, chemical enhancement of the Raman signal, or both. As used herein, the term "SERS-active structure" means any structure configured and formed of a material that may produce enhancement of the Raman signal. The representative SERS-active structure 104 illustrated in FIGS. 1A and 1B includes a mesh or screen formed from metallic rods or wires having a diameter preferably less than about 20 nanometers. Alternative SERS-active structures include, but are not limited to, arbitrarily and selectively arranged particles, dots, columns, rods, columns, pyramids, or any other shape or structure that is capable of enhancing the Raman signal produced by atoms or molecules adsorbed thereon or positioned near thereto, including a simple roughened metal surface.

Exemplary materials for the SERS-active structure 104 include, but are not limited to, gold, silver, copper, aluminum, chromium, platinum, or any other material capable of enhancing the Raman signal produced by atoms or molecules adsorbed on or positioned near the SERS-active structure 104. Although the materials that form the SERS-active structure 104 typically are not transparent to the wavelengths of light used in Raman spectroscopy (about 350 nm to about 1000 nm), the SERS-active structure may be formed with apertures or spaces therethrough (such as the apertures through a screen or mesh) to allow light to pass through the SERS-active structure. In addition, chemical receptors, or chemical species that interact both with the SERS-active structure 104 and the analyte 106 may be provided during operation as known in the art either to promote binding of the analyte 106 to the SERS-active structure 104, or to enhance detection of the analyte 106.

Figure 1B:
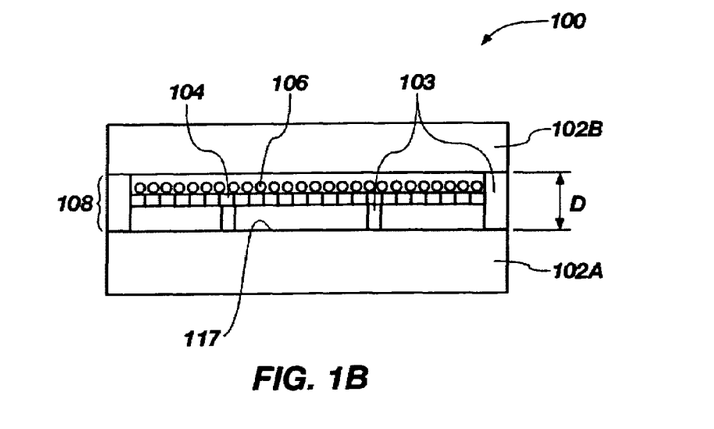
FIG. 1B is a sectional view of the exemplary light amplifying structure of FIG. 1A having spacer elements to provide a predetermined amount of standoff.
Figure 1C:
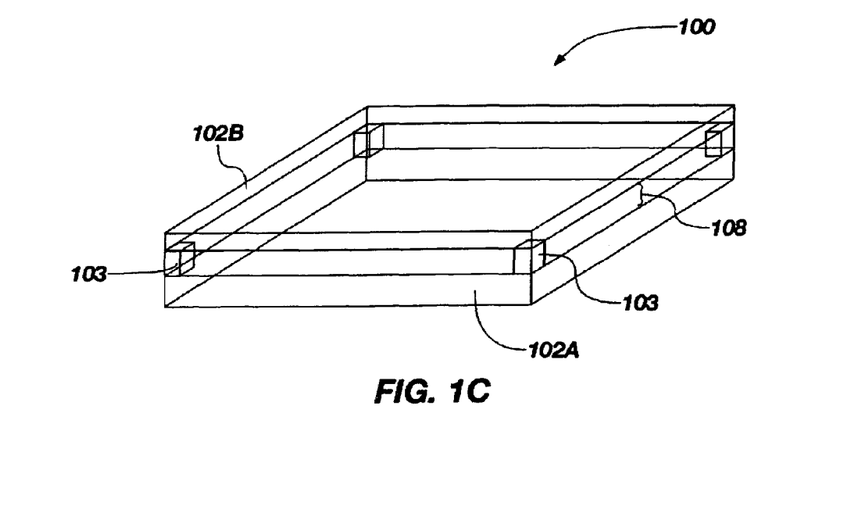
FIG. 1C is a perspective view of the exemplary light amplifying structure of FIG. 1B.

Referring to FIG. 1B, a predetermined amount of standoff between the bottom layer 102A and the top layer 102B may be provided by including spacer elements 103. As shown in FIG. 1C, a plurality of spacer elements 103 may be used, one spacer element being located at each of the corners of the bottom layer 102A and the top layer 102B. As an example, the spacer elements 103 may include epoxy pillars that bond the opposing surfaces of the bottom layer 102A and the top layer 102B together. Alternatively, the spacer elements 103 may include bricks of solder stenciled or screened onto metallic pads (not shown) on the opposing surfaces of the bottom layer 102A and the top layer 102B. The bottom layer 102A and the top layer 102B then may be heated to re-flow the solder, thereby bonding the layers together. Alternatively, the spacer elements 103 may include preformed glass pillars that are bonded to or formed on at least one of the opposing surfaces of the bottom layer 102A and the top layer 102B at the corners thereof. If spacer elements 103 are bonded to the top and bottom layers, an adhesive (e.g., an epoxy or any other suitable adhesive) may be used to bond the materials together. Spacer elements also may be formed directly on the face 117 of the bottom layer 102A.

The SERS-active structure 104 may be located at any position within the resonant cavity 108 using spacer elements 103 to support the SERS-active structure vertically within the cavity, as shown in FIG. 1B. The SERS-active structure 104 may be bonded to the face 117 of the bottom layer 102A or merely disposed thereon.

The bottom layer 102A, the SERS-active structure 104, the top layer 102B, and any spacer elements 103 may be formed separately and attached or secured together, or may be formed separately and merely held together by gravity or weak inter-atomic forces. Alternatively, the bottom layer 102A, the SERS-active structure 104, the top layer 102B, and any spacer elements 103 may be formed layer-by-layer as a monolithic structure using conventional microelectronic fabrication techniques.

The analyte 106 may be provided within the resonant cavity 108 by manually placing the analyte 106 within the resonant cavity 108, or by diffusing the analyte 106 into the resonant cavity 108.

Operation of the light amplifying structure 100 is best described with reference to FIG. 1A. The resonant cavity 108 is a Fabry-Perot resonating cavity. A simple Fabry-Perot resonating cavity may include two parallel, flat, material layers. The bottom layer 102A and top layer 102B function as the material layers of a Fabry-Perot resonator. A resonant cavity 108 is defined between the bottom layer 102A and the top layer 102B. The layers have a refractive index (or dielectric constant) different from that of the resonant cavity 108. When radiation impinges on the upper surface 116 of the top layer 102B in the direction illustrated by direction arrow L in FIG. 1A, at least some of the radiation may pass through the top layer 102B into the resonant cavity 108. The change or difference in refractive index at the interfaces between the bottom layer 102A and the cavity 108, and between the top layer 102B and the cavity 108, may cause at least some of the radiation to be reflected internally within the resonant cavity 108 rather than being transmitted through the layers.

Figure 8A:
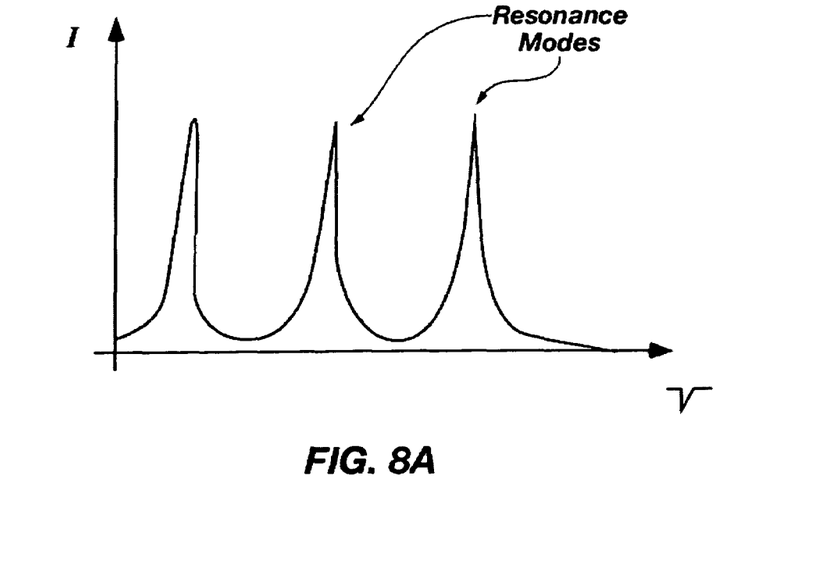
FIG. 8A is an exemplary graph illustrating intensity as a function of wavelength within the resonant cavity of the light amplifying structures of the exemplary embodiments that may function as a Fabry-Perot resonating device.

When the distance D separating the bottom layer 102A and the top layer 102B is equal to an integer number of half wavelengths of the radiation, the internally reflected radiation may interfere constructively, causing the intensity and power of the radiation inside the resonant cavity 108 to increase. When the distance D is not equal to an integer number of half wavelengths of the excitation radiation, the internally reflected light may interfere destructively, causing the intensity of the light inside the resonant cavity 108 to be diminished, which may render the light amplifying structure 100 ineffective for performing SERS. Therefore, for a Fabry-Perot resonant cavity having a distance D, a graph of the intensity of radiation within the resonant cavity as a function of the frequency of the incident radiation may produce a spectrum or plot having a series of peaks corresponding to the resonant frequencies (or resonant modes) of the cavity, similar to that shown by the graph in FIG. 8A. The peaks correspond to wavelengths that satisfy the equation $\lambda = 2D/n$, where $\lambda$ is the wavelength of the incident radiation and n is an integer.

As a result, the distance D must be selected based upon the wavelength of the excitation radiation to be used for SERS in order to increase the intensity of the radiation. For example, if the excitation radiation is to have a wavelength of 800 nanometers, then the distance D may be an integer multiple of 400 nanometers. Therefore D could be 400 nm, 1200 nm, 1600 nm, 2000 nm, 8000 nm, etc.

When the condition for resonance is satisfied, the intensity of the excitation radiation may be increased within the resonant cavity 108 by a factor of about 1000. Therefore, as an example, if the power of the excitation radiation is 1 mW, the power of the radiation resonating within the resonant cavity 108 may be about 1 W. In addition, because the intensity of the radiation inside the resonant cavity can be very high, non-linear effects, such as second harmonic generation, may be appreciable, resulting in increased performance of the light amplifying structure 100.

The intensity of the radiation within the resonant cavity 108 may vary with position. Therefore, the SERS-active structure 104 and the analyte 106 may be positioned at the area of highest radiation intensity within the resonant cavity 108 using the spacer elements 103 (FIG. 1B and 1C). Alternatively, the SERS-active structure 104 and the analyte 106 could be positioned so as to maximize the ratio of the energy stored in the resonant cavity 108 to the energy outside the cavity (i.e. maximize the quality factor (Q-factor) of the cavity).

Reflective coatings (not shown) may be provided on the lower surface 115 of the top layer 102B and the opposing face 117 of the bottom layer 102A. Reflective coatings can be made from silver, diamond, or any other material that will at least partially reflect the incident radiation. The reflective coatings may cause more of the radiation to reflect internally inside the cavity, instead of being transmitted through the dielectric material layers, thereby further increasing the intensity of the radiation resonating within the cavity.

Figure 2:
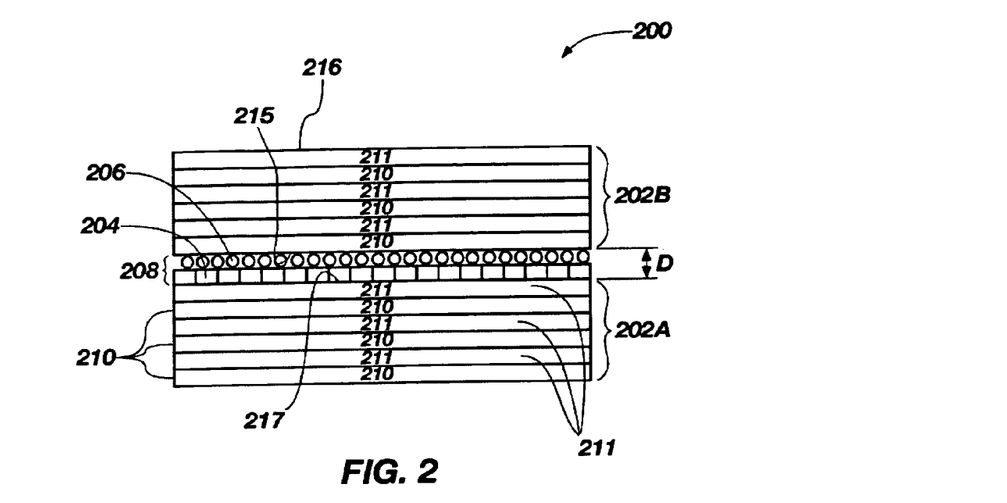
FIG. 2 is a sectional view of an exemplary light amplifying structure that includes Bragg mirrors.

An exemplary light amplifying structure 200 is shown in FIG. 2. The light amplifying structure 200 includes a bottom layer 202A and a top layer 202B that are separated by a distance D to define a standoff or resonant cavity 208 therebetween. The top layer 202B has a lower surface 215 and an upper surface 216 that are generally parallel to each other. Bottom layer 202A has a face 217 opposing the lower surface 215 of the top layer 202B and is separated therefrom by a distance D. A SERS-active structure 204 may be provided between the bottom layer 202A and the top layer 202B within the resonant cavity 208. An analyte 206 may be provided on the SERS-active structure 204 when performing SERS. The distance D may be as small as about a monolayer of the analyte 206 being analyzed or more.

The bottom layer 202A and the top layer 202B of the light amplifying structure 200 may include Bragg mirrors (distributed Bragg reflectors or DBR's), which may be used as the material layers in a Fabry-Perot resonator. Bragg mirrors are highly reflective structures and may have a reflectivity as high as about 99.99%. Bragg mirrors include a multilayer stack of alternating layers of high and low refractive index material, shown in FIG. 2 as low-index layers 210 and high-index layers 211. Reflectivity generally increases with the number of pairs of alternating layers. In the illustrated embodiment, the top layer 202B and the bottom layer 202A each comprise three pairs of layers. However, the top layer 202B and the bottom layer 202A may comprise from one to about sixty pairs of layers, and either the top layer 202B or the bottom layer 202A may comprise more or less pairs of layers than the other layer.

The thickness of each layer may be selected to be approximately one-fourth the wavelength of the incident light divided by the refractive index of the material from which the layer is formed ($\lambda/4n_{ri}$, where $\lambda$ is the wavelength of the incident light and $n_{ri}$ is the refractive index of the material).

Surface enhanced Raman spectroscopy is typically performed using excitation radiation at wavelengths between about 350 nanometers and about 1000 nanometers. Therefore, as an example, if the incident excitation radiation of a SERS system were to have a wavelength of 800 nanometers, and the refractive index of the low-index layers 210 and the high-index layers 211 were 2, the thickness of the low-index layers 210 and the high-index layers 211 may be approximately 100 nanometers. In this configuration, the total thickness of the bottom layer 202A and the top layer 202B would be approximately 600 nanometers (6 layers each having a thickness of 100 nm), and the distance D could be selected to be 400 nm, 1200 nm, 1600 nm, 2000 nm, 8000 nm, etc. (i.e., any integer multiple of one half of 800 nm).

The low-index layers 210 and the high-index layers 211 of the Bragg mirrors may be formed from a variety of materials. As an example, the high-index layers 211 may be formed from GaAs and the low-index layers 210 of AlGaAs. Other examples of suitable material combinations for low-index layers 210 and high-index layers 211 include, but are not limited to: Si and $SiO_2$; AlGaAs layers having alternating atomic percents of Al and Ga; GaN and GaAlN; and GaInAsP and InP. Many such suitable material pairs are known in the art and are intended to be included within the scope of the invention.

The resonant cavity 208 defined by the bottom layer 202A and the top layer 202B of the light amplifying structure 200 may include a Fabry-Perot resonant cavity, and may operate in the same manner discussed previously in relation to the light amplifying structure 100 of FIG. 1.

Bragg mirrors are one-dimensional photonic crystals. Photonic crystals are formed by dispersing a material of one refractive index (or dielectric constant) periodically within a matrix having a different refractive index (or dielectric constant). A one-dimensional photonic crystal is a three-dimensional structure that exhibits periodicity in refractive index in only one dimension. Bragg mirrors are an example of a one-dimensional photonic crystal. The alternating thin layers have different refractive indices. The combination of several thin layers forms a three-dimensional structure that exhibits periodicity in refractive index in the direction orthogonal to the planes of the thin layers. No periodicity is exhibited in directions parallel to the planes of the layers.

A two-dimensional photonic crystal may be formed by periodically dispersing rods, columns, or fibers of a first material having a first refractive index within a matrix of a second material having a second, different refractive index. Two-dimensional photonic crystals exhibit periodicity in only two dimensions, (i.e., the directions perpendicular to the length of the rods or columns), but no periodicity is exhibited in directions parallel to the length of the columns.

Finally, a three-dimensional photonic crystal may be formed by periodically dispersing small spheres or other spatially confined areas of a first material having a first refractive index within a matrix of a second material having a second, different refractive index. Three-dimensional photonic crystals may exhibit periodicity in refractive index in all directions within the crystal.

Figure 8B:
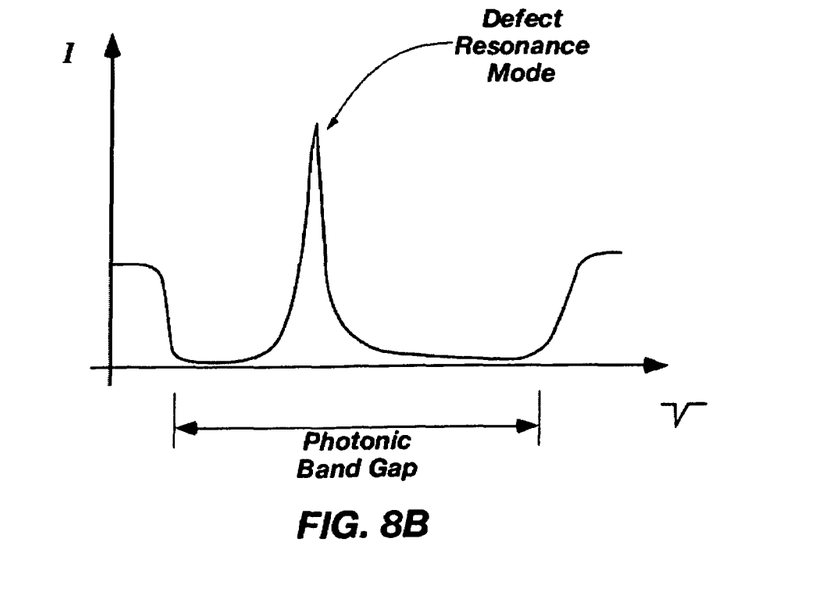
FIG. 8B is an exemplary graph illustrating intensity as a function of wavelength within the resonant cavity of the light amplifying structures of the exemplary embodiments that may function as defect mode associated with a defect in a photonic crystal device.

Photonic crystals may exhibit a photonic bandgap over a range of certain frequencies in the directions exhibiting periodicity in refractive index (see FIG. 8B). In other words, there is a range of frequencies of radiation that will not be transmitted through the crystal in the directions exhibiting periodicity in refractive index. This range of frequencies that are not transmitted is known as the photonic bandgap of the photonic crystal. No photonic bandgap is exhibited in directions that do not exhibit periodicity in refractive index.

When the periodicity in refractive index in a photonic crystal is interrupted, perhaps by a defect or a missing layer in a Bragg mirror, certain defect modes may be generated. A defect may be generated within a photonic crystal by, for example, changing the refractive index within the crystal at a specific location, changing the size of a feature in the crystal, or by removing one feature from the periodic array within the crystal. Defect modes allow certain frequencies of light within the band gap to be partially transmitted through the crystal and enter into the defect area where the photons of the radiation are at least partially trapped or confined. As more photons enter the defect and become trapped or confined, the light intensity may be increased within the cavity, providing a similar intensity amplifying effect as that produced by a Fabry-Perot resonant cavity (FIG. 8B). The frequencies associated with the defect modes are, at least partially, a function of the dimensions of the defect. The finite-difference time-domain method may be used to solve the full-vector time-dependent Maxwell's equations on a computational grid including the macroscopic dielectric function, which will be at least partially a function of the feature dimensions, and corresponding dielectric constant within those features, of the photonic crystal to determine which wavelengths may be forbidden to exist within the interior of any given crystal, and which wavelengths will give rise to a defect mode at the location of a defect within the crystal.

The bottom layer 202A and the top layer 202B of the light amplifying structure 200 of FIG. 2 include one-dimensional photonic crystal Bragg mirrors. The resonant cavity 208 provides a discontinuity or defect in the periodicity in refractive index (and dielectric constant) in the direction perpendicular to the plane of the layers. A photonic band gap may exist in directions passing through the planes of the thin layers. At least one defect mode within the band gap may be generated as a result of the discontinuity of the periodicity in refractive index generated by the resonant cavity 208. The frequency of light corresponding to such a defect mode may be amplified within the interior of the resonant cavity 208, and may be used as the excitation radiation in a SERS system to provide enhanced or increased radiation intensity. Thus, the resonant cavity 208 of the light amplifying structure 200 of FIG. 2 may include both a resonant defect cavity and a Fabry-Perot resonant cavity.

The exemplary SERS-active structure 204 illustrated in FIG. 2 may include an array of microspheres preferably having a diameter less than about 20 nanometers, and may be formed from the same materials described above in relation to the SERS-active structure 104 (FIG. 1A).

Figure 3A:
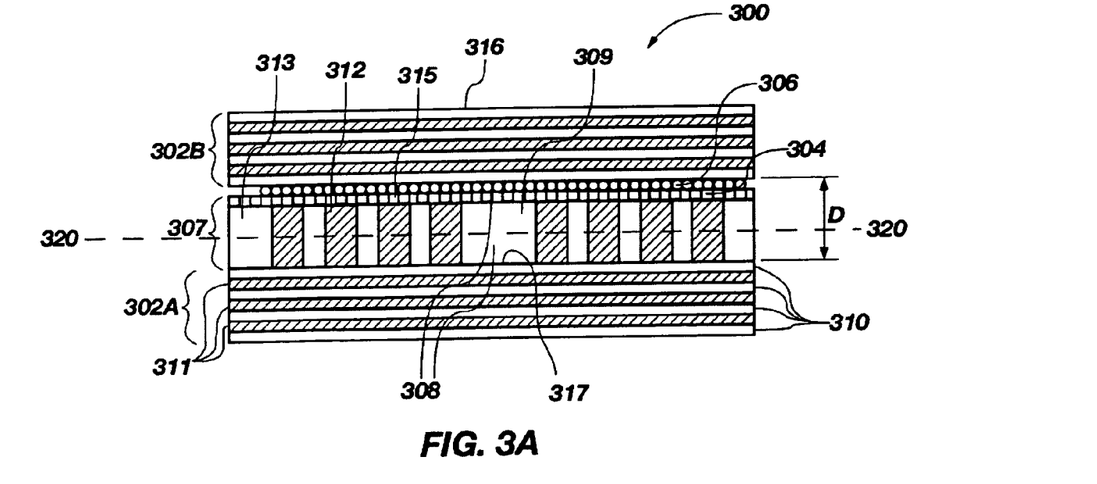
FIG. 3A is a sectional view of an exemplary light amplifying structure that includes Bragg mirrors and a two-dimensional photonic crystal to form part of an resonant cavity.

An exemplary light amplifying structure 300 is shown in FIG. 3A. The light amplifying structure 300 includes a bottom layer 302A and a top layer 302B that are separated by a distance D to define a standoff or resonant cavity 308 therebetween. The top layer 302B has a lower surface 315 and an upper surface 316 that are generally parallel to each other. The bottom layer 302A has a face 317 opposing the lower surface 315 of the top layer 302B and is separated therefrom by a distance D. A SERS-active structure 304 may be provided between the bottom layer 302A and the top layer 302B within the resonant cavity 308. In addition, a cavity layer 307 may be provided between the bottom layer 302A and the top layer 302B. An analyte 306 may be provided on the SERS-active structure 304 when performing SERS. The distance D may be as small as about a monolayer of the analyte 306 being analyzed or more.

The bottom layer 302A and the top layer 302B may include Bragg Mirrors similar to those discussed in relation to the light-amplifying structure 200 of FIG. 2.

Figure 3B:
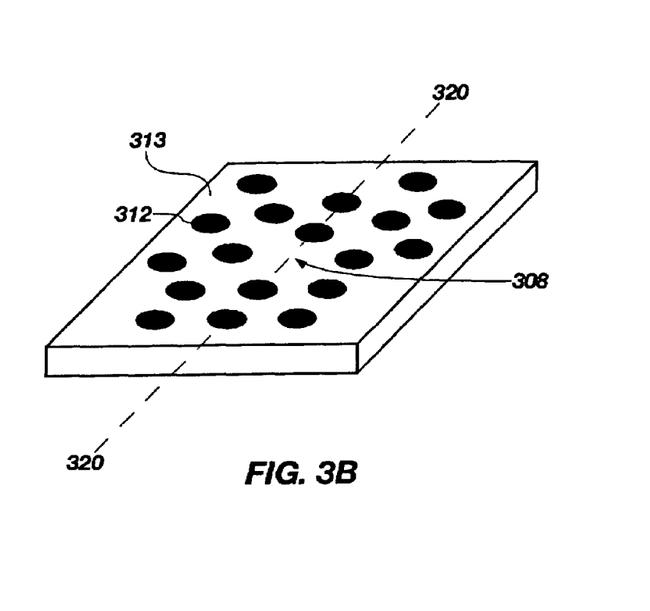
FIG. 3B is a perspective view of the two-dimensional photonic crystal depicted in FIG. 3A.

Referring to FIGS. 3A and 3B, the cavity layer 307 may comprise a two-dimensional photonic crystal with its respective plane of periodicity lying in reference plane 320. The two-dimensional photonic crystal of the cavity layer 307 may be formed by periodically dispersing columns or rods 312 of a first material periodically within a matrix 313 of a second material. However, one rod in the center of the cavity layer 307 is missing, creating a defect cavity 309, as shown in FIG. 3B. Alternatively, the defect cavity 309 could be formed by providing a rod 312 having a diameter greater than or less than the diameter of the other rods 312, or by providing an air gap or a spatially confined area of a different material such as glass or epoxy within the crystal. At least a portion of the standoff between the top surface of the cavity layer 307 and the lower surface 315 of the top layer 302B, and the defect cavity 309, collectively define the resonant cavity 308.

Examples of suitable materials for the columns or rods 312 and the matrix 313 in which they are disposed include, but are not limited to: GaAs and AlGaAs; AlGaAs columns within an AlGaAs matrix having different atomic percents of Al and Ga; GaN and GaAlN; Si and $SiO_2$; Si and SiN; and GaInAsP and InP. In practice, virtually any two materials that have different refractive indices may be used.

It is not necessary for the cavity layer 307 to be formed as a two-dimensional photonic crystal. Any layer containing a suitable defect cavity 309 may be used as the cavity layer 307. For example, a silica microsphere may be embedded in a layer comprising a matrix of material, such as silicon, having a different refractive index than that of the silica.

Although not shown in FIG. 3A, spacer elements identical to spacer elements 103 (FIG. 1B) may be used to provide a predetermined amount of standoff (thereby increasing the distance D) between the opposing surfaces of the cavity layer 307 and the top layer 302B.

The resonant cavity 308 of the light amplifying structure 300 of FIG. 3 operates in a similar fashion to the light amplifying structure 200 of FIG. 2, and may amplify the incident light in two ways. For example, the structure may operate as a Fabry-Perot resonating cavity when the wavelength of the incident light is an integer multiple of one half of the distance separating the lower layer 302A and the upper layer 302B, as discussed previously in relation to the light amplifying structure 100 of FIG. 1. Alternatively, the incident light may be amplified when the wavelength of the incident radiation corresponds to a defect mode generated by the resonant cavity between the Bragg mirrors, which creates a discontinuity in the periodicity in refractive index of the one dimensional photonic crystal Bragg mirrors, as described previously in relation to the light amplifying structure 200 of FIG. 2.

The cavity layer 307 may be used to laterally confine the excitation radiation, which has entered the resonant cavity 308 through the Bragg mirrors of the bottom layer 302A or the top layer 302B, within the area proximate the resonant cavity 308, the SERS-active structure 304, and the analyte 306, thereby preventing the excitation radiation from propagating in any direction contained within the reference plane 320. The cavity layer 307, which includes a two-dimensional photonic crystal, may exhibit a photonic band gap over a range of frequencies in any direction contained within the reference plane 320. In addition, the cavity layer 307 may exhibit defect modes associated with the defect cavity 309. Therefore, radiation having a frequency within the photonic band gap of cavity layer 307 will not be transmitted through the layer in any direction within the reference plane 320, and may be reflected by the cavity layer 307. Therefore, the wavelength or frequency of the excitation radiation may be selected to be within the photonic band gap of the two-dimensional photonic crystal of the cavity layer 307 (or the cavity layer 307 may be designed to exhibit a photonic bandgap over the range of wavelengths of the desired excitation radiation). In this manner, the efficiency of the light amplifying structure 300 may be increased relative to the light amplifying structures 100 (FIGS. 1A-1C) and 200 (FIG. 2).

Figure 4:
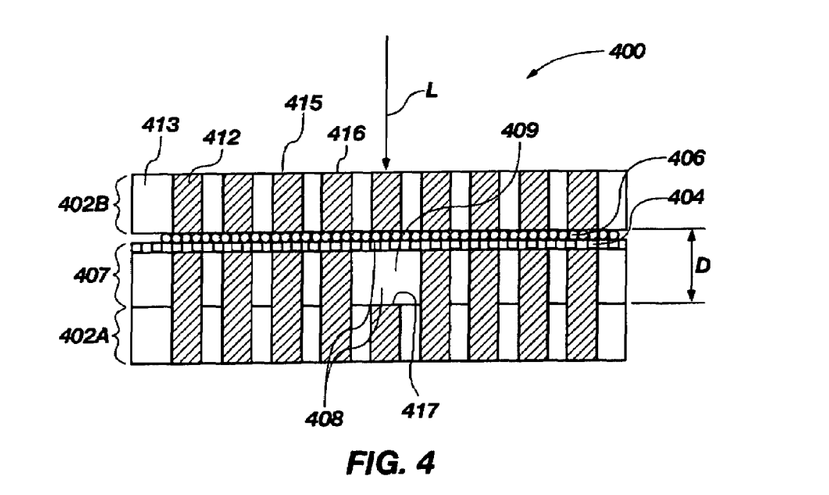
FIG. 4 is a sectional view of an exemplary light amplifying structure that includes multiple two-dimensional photonic crystals.

An exemplary light amplifying structure 400 is shown in FIG. 4. The light amplifying structure 400 includes a bottom layer 402A and a top layer 402B that are separated by a distance D to define a standoff or resonant cavity 408 therebetween. The top layer 402B has a lower surface 415 and an upper surface 416 that are generally parallel to each other. The bottom layer 402A has a face 417 opposing the lower surface 415 of the top layer 402B and is separated therefrom by a distance D. A SERS-active structure 404 may be provided between the bottom layer 402A and the top layer 402B within the resonant cavity 408. In addition, a cavity layer 407 may be provided between the bottom layer 402A and the top layer 402B. An analyte 406 may be provided on the SERS-active structure 404 when performing SERS. The distance D may be as small as about a monolayer of the analyte 406 being analyzed or more.

The bottom layer 402A and the top layer 402B each may include a two-dimensional photonic crystal. The two-dimensional photonic crystals may be formed by periodically dispersing columns or rods 412 of a first material periodically within a matrix 413 of a second material. Examples of suitable materials for the columns or rods 412 and the matrix 413 in which they are disposed include, but are not limited to: GaAs and AlGaAs; AlGaAs columns within an AlGaAs matrix having different atomic percents of Al and Ga; GaN and GaAlN; Si and $SiO_2$; Si and SiN; and GaInAsP and InP. Many such materials are known in the art, and, in practice, virtually any two materials that have different refractive indices may be used.

The light amplifying structure 400 also may include a cavity layer 407 disposed between the bottom layer 402A and the top layer 402B. Cavity layer 407 may be identical to the cavity layer 307, which was previously described in relation to the light amplifying structure 300 (FIGS. 3A and 3B). Cavity layer 407 may include a defect cavity 409, identical to the defect cavity 309, which was previously described in relation to the light amplifying structure 300 (FIGS. 3A and 3B). A resonant cavity 408 is collectively defined by the defect cavity 409 and at least a portion of the volume of the standoff between the top surface of the cavity layer 407 and the lower surface 415 of the top layer 402B.

Spacer elements (not shown) identical to spacer elements 103 of FIG. 1B may be used to provide a predetermined amount of standoff between the opposing surfaces of the cavity layer 307 and the top layer 302B, thereby changing the distance D.

The bottom layer 402A and top layer 402B may operate as the material layers of a Fabry-Perot resonating device in the same way described above in reference to the light amplifying structure 100 of FIG. 1A. Excitation radiation entering the light amplifying structure 400 in the direction L shown in FIG. 4 may resonate within the resonant cavity 408 when the distance D is equal to an integer multiple of one half of the wavelength of the excitation radiation.

Because the bottom layer 402A, the top layer 402B and the cavity layer 407 each are formed as two-dimensional photonic crystals exhibiting periodicity in refractive index in the directions parallel to the planes of each layer, each layer may exhibit a photonic band gap in any such direction. If the bottom layer 402A, the top layer 402B, and the cavity layer 407 are designed to exhibit a photonic bandgap that includes the wavelength or frequency of the excitation radiation, the excitation radiation may be locally confined to the area in the vicinity of the defect cavity 409, and the portion of the analyte 406 adjacent thereto, thereby further increasing the intensity of the excitation radiation in the vicinity of the resonant cavity 408.

In addition, the cavity layer 407 may exhibit defect modes within the photonic bandgap that are associated with the defect cavity 409. If excitation radiation having a wavelength that corresponds to the defect mode is incident on a side of the structure instead of on the top or bottom of the structure, the radiation may resonate, increasing the intensity thereof, in the vicinity of the defect cavity 409.

The bottom layer 402A and the top layer 402B of the light amplifying structure 400 shown in FIG. 4 alternatively may comprise three-dimensional photonic crystals, which may comprise small spheres or other spatially confined areas of a first material having a first refractive index periodically dispersed within a matrix of a second material having a second, different, refractive index. Three-dimensional photonic crystals may be formed by stacking two-dimensional photonic crystals in an offset configuration. For example, the rods of one layer may be located directly above a matrix region of the layer below. Multiple layers may be stacked to create a three-dimensional photonic crystal structure. Such three-dimensional photonic crystals exhibit periodicity in refractive index in all three dimensions within the crystal.

The bottom layer 402A, the SERS-active structure 404, the top layer 402B, and any spacer elements 103 may be formed separately and attached or secured together, or may be formed separately and merely held together by gravity or weak inter-atomic forces. Alternatively, the bottom layer 402A, the SERS-active structure 404, the top layer 402B, and any spacer elements 103 may be formed layer-by-layer as a monolithic structure using conventional microelectronic fabrication techniques.

Figure 5:
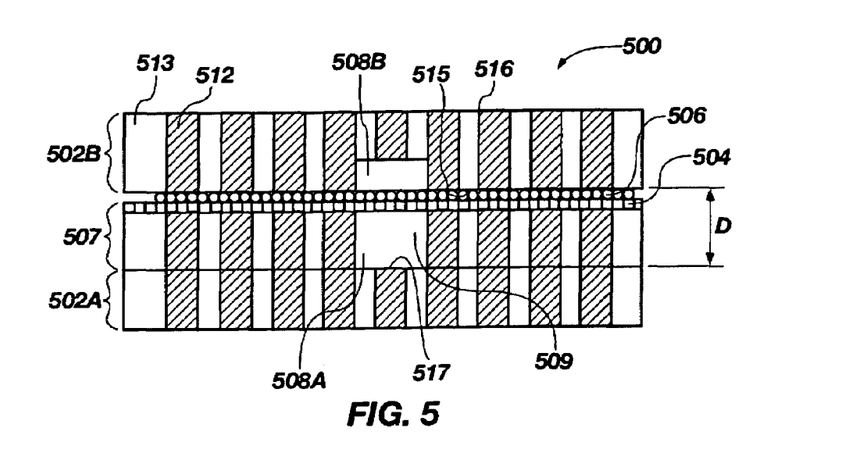
FIG. 5 is a sectional view of another exemplary light amplifying structure wherein the SERS-active structure is situated at a predetermined location within the resonant cavity.

An exemplary light amplifying structure 500 is shown in FIG. 5. The light amplifying structure 500 includes a bottom layer 502A and a top layer 502B that are separated by a distance D to define a standoff or resonant cavity 508 therebetween. The top layer 502B has a lower surface 515 and an upper surface 516 that are generally parallel to each other. The bottom layer 502A has a face 517 opposing the lower surface 515 of the top layer 502B and is separated therefrom by a distance D. A SERS-active structure 504 may be provided between the bottom layer 502A and the top layer 502B within the resonant cavity 508. In addition, a cavity layer 507 may be provided between the bottom layer 502A and the top layer 502B. An analyte 506 may be provided on the SERS-active structure 504 when performing SERS. The distance D may be as small as about a monolayer of the analyte 506 being analyzed or more.

The bottom layer 502A and the top layer 502B are substantially identical to the bottom layer 402A and the top layer 502B described previously in relation to the light amplifying structure 400 of FIG. 4. However, the top layer 502A includes a partial defect cavity 508B, which may be substantially identical to the defect cavities described previously herein.

The light amplifying structure 500 also may include a cavity layer 507 disposed between the bottom layer 502A and the top layer 502B. Cavity layer 507 may be identical to the cavity layer 307, which was previously described in relation to the light amplifying structure 300 (FIGS. 3A and 3B). Cavity layer 507 may include a defect cavity 509, identical to the defect cavity 309, which was previously described in relation to the light amplifying structure 300 (FIGS. 3A and 3B).

A resonant cavity 508 may be collectively defined by the partial defect cavity 508B formed in the top layer 502B and the partial resonant cavity 508A. The partial resonant cavity 508A includes the defect cavity 509 of the cavity layer 507 and at least a portion of the volume or standoff between the lower surface 515 of the top layer 502B and the top surface of the cavity layer 507.

In this configuration, the SERS-active structure 504 may be located at an optimal position within the resonant cavity 508. As previously described, the intensity of the radiation within a resonant cavity may vary with position. The quality factor, or Q-factor, is defined as the ratio of the energy stored in the resonant cavity to the energy outside the cavity, and may be used to describe the ability of the resonant cavity to increase the intensity of radiation therein. Disposing the SERS-active structure 504 and the analyte 506 at different positions within the resonant cavity 508 may alter the quality factor of the resonant cavity. Therefore, the SERS-active structure 504 and the analyte 506 may be positioned so as to compromise between maximizing the quality factor and positioning the SERS-active structure 504 and the analyte 506 at an area of maximized radiation intensity. The optimal position within the resonant cavity 508 will provide the highest intensity of excitation radiation in the vicinity of the analyte 506 disposed adjacent at least a portion of the SERS-active structure 504. The strength of the signal produced by Raman scattered photons may be optimized by positioning the SERS-active structure 504 and the analyte 506 at such a location within the resonant cavity 508.

The light amplifying structure 500 of FIG. 5 may operate in substantially the same manner previously described in relation to the light amplifying structure 400 of FIG. 4.

Figure 6A:
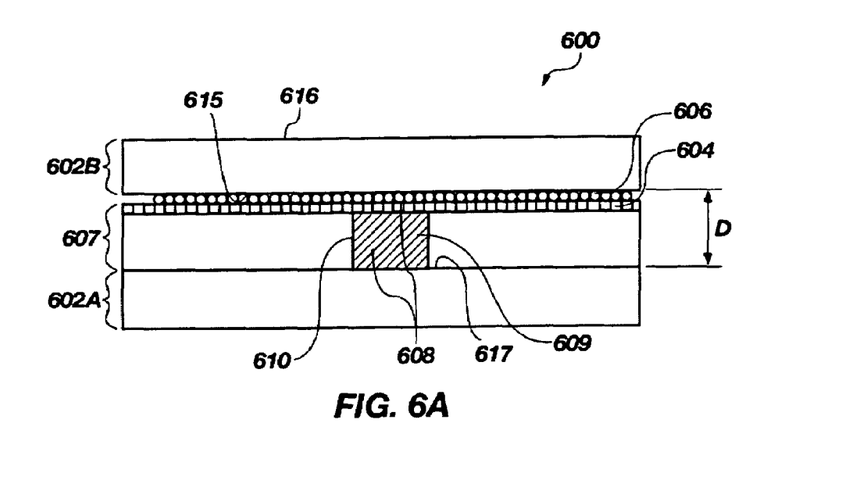
FIG. 6A is a schematic sectional view of an exemplary light amplifying structure having a cavity layer.

An exemplary light amplifying structure 600 is shown in FIG. 6A. The light amplifying structure 600 includes a bottom layer 602A and a top layer 602B that are separated by a distance D to define a standoff or resonant cavity 608 therebetween. The top layer 602B has a lower surface 615 and an upper surface 616 that are generally parallel to each other. The bottom layer 602A has a face 617 opposing the lower surface 615 of the top layer 602B and is separated therefrom by a distance D. A SERS-active structure 604 may be provided between the bottom layer 602A and the top layer 602B within the resonant cavity 608. In addition, a cavity layer 607 may be provided between the bottom layer 602A and the top layer 602B. An analyte 606 may be provided on the SERS-active structure 604 when performing SERS. The distance D may be as small as about a monolayer of the analyte 606 being analyzed or more.

The bottom layer 602A and the top layer 602B may be formed from a first dielectric material having a first refractive index. The cavity layer 607 may be formed from the same material as the bottom layer 602A and the top layer 602B, and may include a defect cavity 609, which may be formed as a spatially confined area of a second dielectric material or as a void (e.g., a void containing air) having a second refractive index embedded in the first dielectric material. For example, the defect cavity 609 may be formed as a silica microsphere embedded in the first dielectric material of the cavity layer 607.

Figure 6B:
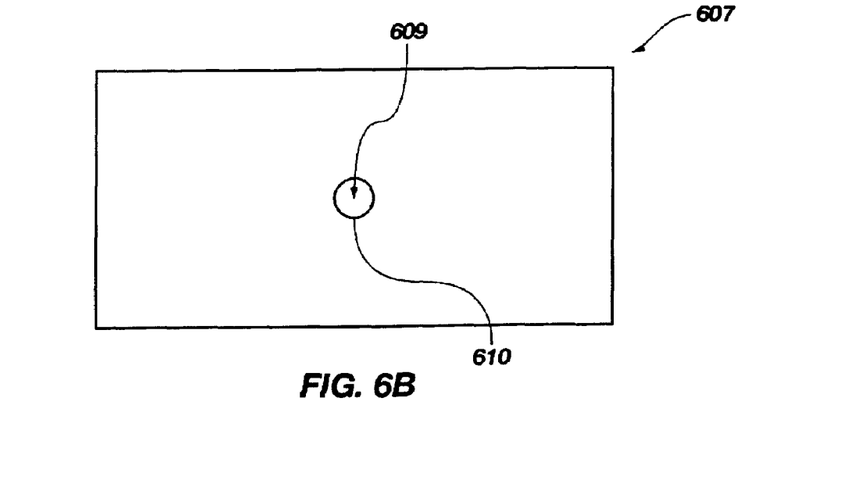
FIG. 6B is a plan view of the cavity layer and the resonant cavity of the light amplifying structure of FIG. 6A.

One example of a configuration that may be used for the cavity 609 is illustrated in the plan view of cavity layer 607, shown in FIG. 6B. The cavity 609 is depicted as a generally cylindrical structure having a surface 610. The surface 610 defining the boundary between the first dielectric material of the cavity layer 607 and the cavity 609 may comprise multiple pairs of adjacent cylindrical layers of alternating refractive indices to form a cylindrical Bragg Mirror, similar to those discussed previously in relation to the light amplifying structure 200, and may be formed of the same materials.

As in the previous embodiments, the defect cavity 609 and at least a portion of the volume or the standoff between the lower surface 515 of the top layer 602B and the upper surface of the cavity layer 607 collectively define a resonant cavity 608. As with the aforementioned embodiments, the SERS-active structure 604 may be positioned so that it is located at an optimal position within the resonant cavity 608.

The bottom layer 602A and top layer 602B may operate as the material layers of a Fabry-Perot resonating device in the same way described above in reference to the light amplifying structure 100 of FIG. 1A. Excitation radiation entering the light amplifying structure 600 may resonate within the resonant cavity 608 when the distance D is equal to an integer multiple of one half of the wavelength of the excitation radiation.

All features of the light amplifying structures 100, 200, 300, 400, 500, and 600, including the bottom layer, the top layer, spacer elements, SERS-active structures, cavity layers, and Bragg mirror layers may be formed using conventional microelectronic fabrication techniques on a support substrate such as, for example, a silicon wafer, partial wafer, or a glass substrate. Examples of techniques for depositing material layers include, but are not limited to, molecular beam epitaxy (MBE), atomic layer deposition (ALD), chemical vapor deposition (CVD), physical vapor deposition (PVD), sputter deposition and other known microelectronic layer deposition techniques. Photolithography may also be used to form structures in layers, such as a cavity in a cavity layer. Examples of techniques that can be used for selectively removing portions of the layers include, but are not limited to, wet etching, dry etching, plasma etching, and other known microelectronic etching techniques. These techniques are known in the art and will not be further described herein.

If desired, the bottom layer and the top layer of the light amplifying structures disclosed herein may be formed on a support substrate such as, for example, a silicon wafer, partial wafer, or a glass substrate. A portion of the support substrate may then be removed, for example, by way of etching, to expose the bottom layer or the top layer. If the support substrate is optically transparent for the wavelengths of incident light employed in the SERS system, none of the support substrate needs to be removed.

In addition, each of the bottom layer, top layer, spacer elements, SERS-active structures, cavity layers, and Bragg mirror layers may be formed separately and assembled together, or alternatively, two or more of the structures may be formed together, for example, by forming one layer or element on top of another layer or element.

Figure 7A:
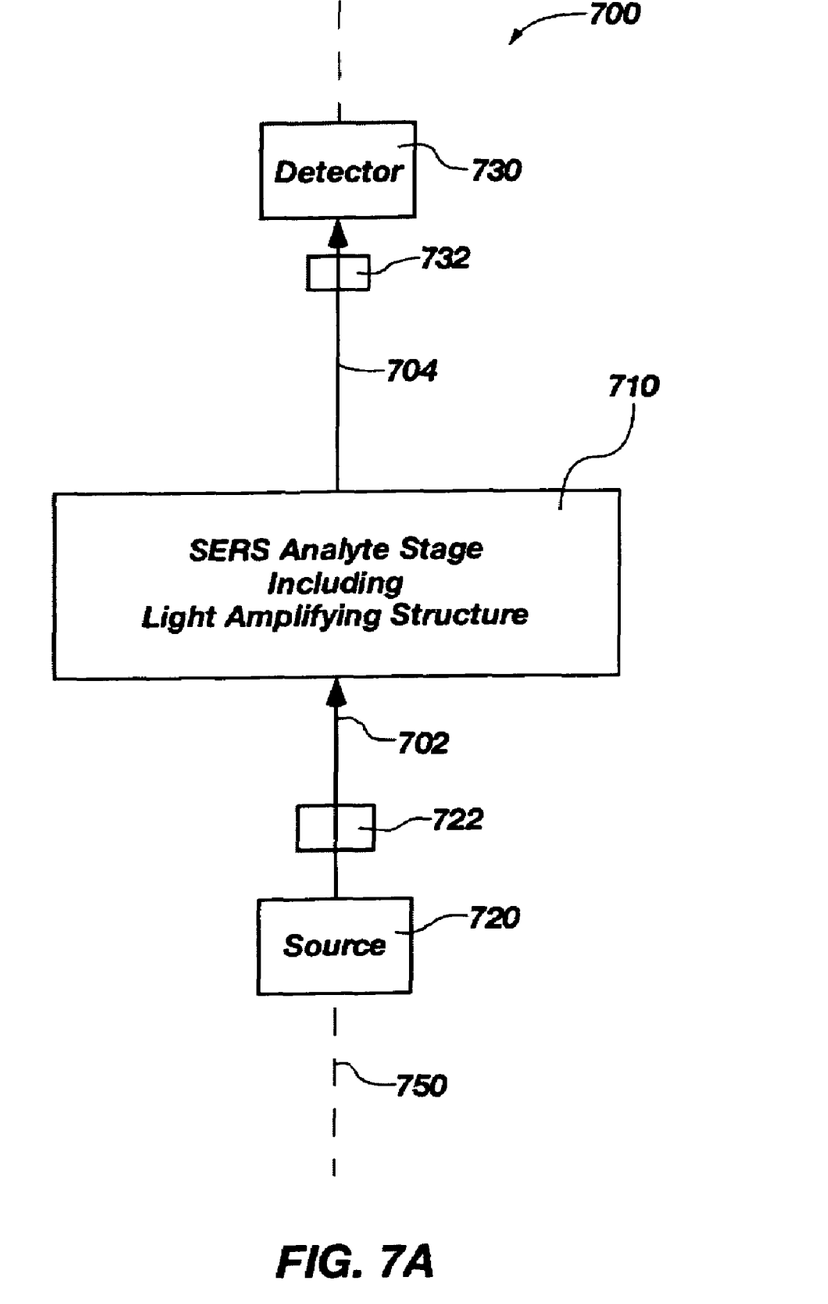
FIG. 7A is a schematic illustration of an exemplary SERS system that may employ any one of the light amplifying structures of FIGS. 1 through 6.

Referring to FIG. 7A, an exemplary SERS system 700 includes a SERS sample or analyte stage 710 that includes any one of the light amplifying structures 100, 200, 300, 400, 500, or 600 disclosed herein, or an equivalent thereof, an excitation radiation or light source 720, and a detector 730. The SERS system 700 may also include various optical components 722 between the light source 720 and the analyte stage 710, and various optical components 732 between the analyte stage 710 and the detector 730.

The light source 720 may be any suitable light source configured for emitting light in the desired wavelength and, preferably, having a tunable wavelength. As an example, commercially available semiconductor lasers, helium-neon lasers, carbon dioxide lasers, light emitting diodes, incandescent lamps, and many others may be used as the light source 710. The wavelengths that are emitted by the light source 720 employed in the SERS system 700 of the present invention may be any suitable wavelength for properly analyzing the analyte contained within the light amplifying structure of the analyte stage 710. As an example, a representative range for the wavelengths that may be emitted by the light source 720 includes frequencies from about 350 nm to about 1000 nm.

The light 702 from the light source 720 may be delivered directly from the light source 720 to the analyte stage 710. Alternatively, collimation, filtration, and subsequent focusing of light 702 with optical components 722 may be performed before the light 702 impinges on a surface of the light amplifying structure of the analyte stage 710. The light amplifying structure of the analyte stage may be oriented in any direction relative to the impinging light 702 that allows the light to be amplified within the light amplifying structure, but is preferably oriented so that the light impinges on either a top layer or bottom layer of the light amplifying structure in a direction perpendicular thereto (e.g., in the direction L shown in FIG. 1A).

The light amplifying structure of the analyte stage 710 may increase the intensity of the excitation radiation or light 702 within a resonant cavity, as discussed previously with respect to each of the embodiments of the invention. This amplified excitation radiation will impinge on both the SERS-active structure and the analyte disposed adjacent the SERS-active structure near (or within) the resonant cavity of the light amplifying structure. The irradiation of the SERS-active structure by the amplified light produces a surface enhancement effect therein (i.e., chemical, electromagnetic, or both). In other words, irradiation of the SERS-active structure by amplified light 702 may produce a strong electromagnetic field near the SERS-active structure. The analyte adjacent the portion of the SERS-active structure that is being irradiated by amplified light 702, in turn, experiences this very strong electromagnetic field. At least a portion of the amplified radiation may impinge on the analyte and may be inelastically scattered as Stokes or anti-Stokes radiation (or both) to produce Raman scattered photons 704. The electromagnetic field enhances the intensity of the signal produced by Raman photons 704 scattered by the analyte. Because the intensity of the Raman photons 704 scattered by the analyte is, in part, proportional to the square of the electromagnetic field experienced by the analyte, the enhancement effect from the SERS-active structure may increase the intensity of the signal of the Raman scattered photons 704 by as much as $10^{14}$.

The Raman scattered photons 704 scattered by the analyte or sample may be collimated, filtered, or focused with optical components 732. For example, a filter or a plurality of filters may be employed, either included, with the structure of the detector 730, or as a separate unit that is configured to filter the wavelength of the light 702 from the light source 720, thus allowing only the Raman scattered photons 704 to be received by the detector 730.

The detector 730 receives and detects the Raman scattered photons 704 and may include a monochromator (or any other suitable device for determining the wavelength of the Raman scattered photons 704) and a device such as, for example, a photomultiplier for determining the quantity or number of the emitted Raman scattered photons (intensity). If desired, the detector 730 may also be positioned on the same side of the analyte stage 710 as the light source 720 to receive Raman scattered photons 704.

Figure 7B:
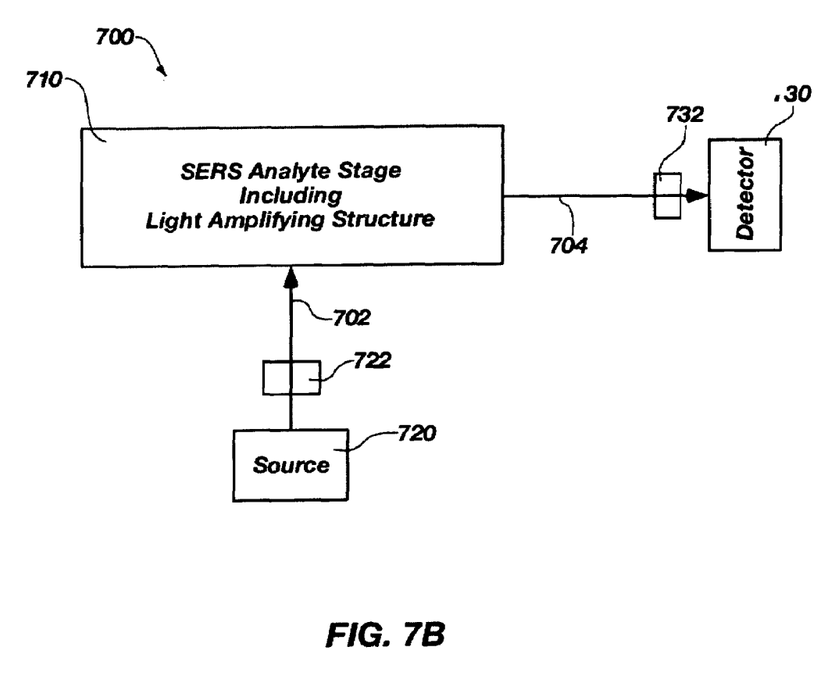
FIG. 7B is a schematic illustration of another exemplary SERS system that may employ any one of the light amplifying structures of FIGS. 1 through 6 wherein the detector is oriented 90 degrees relative to the direction of the incident light.

Ideally, the Raman scattered photons 704 are isotropic, being scattered in all directions relative to the analyte stage 710. Thus, the position of detector 730 relative to the analyte stage 710 is not particularly important. However, the detector 730 may be positioned at, for example, an angle of 90° relative to the direction of the incident light 702 to minimize the intensity of the incident light 702 that may be incident on the detector 730, as shown in FIG. 7B.

In another exemplary embodiment, the wave vector of the incident light 702 may be slightly off-axis relative to the reference axis 750 (FIG. 7A) and the detector 730 positioned to receive the Raman-scattered photons 704 having a wave vector parallel to the reference axis 750. In such a configuration, the light 702 from the light source 720 will be substantially filtered and the detector 730 will only receive the Raman-scattered photons 704.

Because the intensity of the incident light 702 is increased or amplified within the light amplifying structures of the analyte stage 710 in the SERS system 700, the light source 720 need not be as powerful as those required in conventional SERS systems. This, in turn, enables the SERS system 700 to be smaller and portable compared to the relatively large conventional SERS systems. Furthermore, the SERS system 700 is capable of performing more sensitive chemical analysis and consumes less power than conventional SERS systems.

By amplifying the intensity of the excitation radiation using the structures, systems, and methods disclosed herein, a low-power radiation source may be used. Low-power radiation sources are smaller, portable, cost less, and are cheaper to operate than conventional high-power radiation sources typically used in spectroscopic systems. In addition, the strength of the detected Raman signal is proportional to the intensity of the incident excitation radiation. Therefore, a stronger signal from inelastically scattered radiation emitted from the excited analyte can be produced and detected when using the resonant cavities of the present invention in typical spectroscopic analysis systems with conventional excitation radiation sources. A stronger signal from inelastically scattered radiation emitted from the excited analyte also allows for more sensitive and accurate chemical analysis of the analyte (e.g., detection or analysis of single molecules), including its chemical state and physical properties.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A light amplifying structure for surface-enhanced Raman spectroscopy (SERS), comprising:
   a first portion having a first surface and an opposing second surface;
   a second portion having a face opposing the first surface of the first portion with a resonant cavity provided therebetween; and
   a SERS-active structure disposed between the first portion and the second portion within the resonant cavity, wherein the first portion and the second portion of the light amplifying structure each comprise a Bragg Mirror.

2. The light amplifying structure of claim 1, wherein the light amplifying structure further comprises spacer elements disposed between the first portion and the second portion.

3. The light amplifying structure of claim 1, wherein the light amplifying structure further comprises a cavity layer disposed between the first portion and the second portion, the cavity layer having a defect cavity therein proximate the SERS-active structure.

4. The light amplifying structure of claim 3, wherein the cavity layer comprises a two-dimensional (2-D) photonic crystal, the 2-D photonic crystal exhibiting periodicity in refractive index in all directions parallel to the plane of the cavity layer.

5. The light amplifying structure of claim 3, wherein the cavity layer comprises a first dielectric material.

6. The light amplifying structure of claim 5, wherein the defect cavity comprises a second dielectric material, the refractive index of the second dielectric material being different than the refractive index of the first dielectric material.

7. The light amplifying structure of claim 5, wherein the defect cavity includes a boundary between the first dielectric material and the defect cavity, the boundary comprising a Bragg Mirror.

8. The light amplifying structure of claim 3, wherein the cavity layer and at least one of the first portion and the second portion are formed as a monolithic structure.

9. The light amplifying structure of claim 3, wherein one of the first portion and the second portion comprises an additional defect cavity, the defect cavity together with the additional defect cavity define the resonant cavity of the light amplifying structure.

10. The light amplifying structure of claim 1, wherein the SERS-active structure comprises a material selected from the group consisting of Au, Ag, Cu, Na, K, Cr, Al, and Li.

11. The light amplifying structure of claim 1, wherein the SERS-active structure comprises at least one nanowire having a diameter less than about 20 nanometers.

12. The light amplifying structure of claim 1, wherein at least a portion of the SERS-active structure is positioned between the first portion and the second portion within the resonant cavity.

13. A light amplifying structure for surface-enhanced Raman spectroscopy (SERS), comprising:
a first portion having a first surface and an opposing second surface;
a second portion having a face opposing the first surface of the first portion with a resonant cavity provided therebetween; and
a SERS-active structure disposed between the first portion and the second portion within the resonant cavity, wherein the first portion and the second portion each comprise a two-dimensional (2-D) photonic crystal.

14. The light amplifying structure of claim 13, wherein the SERS-active structure comprises a material selected from the group consisting of Au, Ag, Cu, Na, K, Cr, Al, and Li.

15. The light amplifying structure of claim 13, wherein the resonant cavity comprises a Fabry-Perot resonant cavity.

16. A surface-enhanced Raman spectroscopy (SERS) system, comprising:
a light amplifying structure comprising:
a first portion having a first surface and an opposing second surface;
a second portion having a face opposing the first surface of the first portion with a resonant cavity provided therebetween; and
a SERS-active structure located between the first portion and the second portion within the resonant cavity;
a light source configured to irradiate light onto a surface of the light amplifying structure; and
a detector configured to receive Raman-scattered light scattered by an analyte located within the resonant cavity and adjacent the SERS-active structure, wherein the first portion and the second portion of the light amplifying structure each comprise a Bragg Mirror.

17. The SERS system of claim 16, wherein the light source is configured to irradiate light substantially perpendicular to the plane of the first surface of the first portion of the light amplifying structure.

18. The SERS system of claim 16, wherein the detector is configured to detect Raman scatted light scattered by the analyte at an angle substantially perpendicular to the direction of the light emitted by the light source.

19. The SERS system of claim 16, wherein the detector is configured to detect Raman scatted light scattered by the analyte in a direction substantially parallel to the direction of the light emitted by the light source.

20. The SERS system of claim 16, further comprising optical components disposed between the light amplifying structure and at least one of the detector and the light source.

21. A surface enhanced Raman spectroscopy (SERS) system, comprising:
a light-amplifying structure comprising
a first portion having a first surface and an opposing second surface;
a second portion having a face opposing the first surface of the first portion with a resonant cavity provided therebetween; and
a SERS-active structure located between the first portion and the second portion, wherein the first portion and the second portion each comprise a two-dimensional (2-D) photonic crystal;
a light source configured to irradiate a surface of the light amplifying structure; and
a detector configured to receive Raman scattered light scattered by an analyte when the analyte is located adjacent the SERS-active structure.

22. The SERS system of claim 21, wherein the SERS-active structure comprises it material selected from the group consisting of Au, Ag, Cu, Na, K, Cr, Al, and Li.

23. The SERS system of claim 21, wherein the amplifying light structure comprises a Fabry-Perot resonant cavity.

24. A method of performing surface enhanced Raman spectroscopy (SERS), comprising:
providing a radiation-amplifying structure comprising:
a first portion having a first surface and an opposing second surface;
a second portion having a face opposing the first surface of the first portion with a resonant cavity provided therebetween; and
a SERS-active structure located between the first portion and the second portion, wherein the first portion and the second portion of the light amplifying structure each comprise a Bragg Mirror or a two-dimensional (2-D) photonic crystal;
providing an analyte adjacent the SERS-active structure;
irradiating a surface of the radiation amplifying structure with incident radiation;
amplifying the intensity of the incident radiation with the means for amplifying radiation to produce amplified radiation, the amplified radiation irradiating the SERS-active structure and the analyte so as to effect Raman scattering of the amplified radiation by the analyte; and
detecting the Raman scattered radiation.

25. The method of claim 24, wherein the radiation-amplifying structure comprises at least one of a Fabry-Perot resonant cavity and a resonant cavity within a photonic crystal.

26. The method of claim 25, further comprising:
selecting the wavelength of the incident radiation to correspond to a resonance mode of the resonant cavity.

27. The method of claim 24, wherein detecting Raman scattered radiation comprises providing a detector positioned relative to the radiation amplifying structure to receive the Raman scattered radiation, the method further comprising filtering certain wavelengths of radiation from the radiation being received by the detector.

28. The method of claim 24, wherein providing an analyte adjacent the SERS-active structure comprises placing the analyte adjacent the SERS-active structure.

29. The method of claim 24, wherein the providing an analyte adjacent the SERS-active structure comprises diffusing the analyte onto the SERS-active structure.

30. The method of claim 24, wherein the Raman scattered radiation is scattered by a single molecule.

31. The light amplifying structure of claim 13, wherein the SERS-active structure comprises at least one nanowire having a diameter less than about 20 nanometers.

32. The light amplifying structure of claim 13, wherein at least a portion of the SERS-active structure is positioned between the first portion and the second portion within the resonant cavity.

* * * * *

UNITED STATES PATENT AND TRADEMARK OFFICE
CERTIFICATE OF CORRECTION

PATENT NO.         : 7,339,666 B2  
APPLICATION NO. : 10/942079  
DATED                 : March 4, 2008  
INVENTOR(S)       : Shih-Yuan Wang et al.

It is certified that error appears in the above-identified patent and that said Letters Patent is hereby corrected as shown below:

In column 18, line 4, in Claim 18, delete "scatted" and insert -- scattered --, therefor.

In column 18, line 8, in Claim 19, delete "scatted" and insert -- scattered --, therefor.

In column 18, line 32, in Claim 22, delete "it" and insert -- a --, therefor.

Signed and Sealed this

Fourteenth Day of July, 2009

JOHN DOLL  
*Acting Director of the United States Patent and Trademark Office*